United States Patent [19]

Ohdan et al.

[11] Patent Number: 5,688,984

[45] Date of Patent: Nov. 18, 1997

[54] POROUS LITHIUM ALUMINATE CARRIER OF SPINEL STRUCTURE FOR CATALYST

[75] Inventors: Kyoji Ohdan; Tokuo Matsuzaki; Mikio Hidaka, all of Yamaguchi, Japan

[73] Assignee: Ube Industries, Ltd., Yamaguchi, Japan

[21] Appl. No.: 652,729

[22] Filed: May 22, 1996

[30] Foreign Application Priority Data

May 22, 1995 [JP] Japan ................................. 7-146835
Jun. 28, 1995 [JP] Japan ................................. 7-184907

[51] Int. Cl.[6] ................................................. C07C 69/96
[52] U.S. Cl. ........................... 558/277; 558/260; 558/274
[58] Field of Search ................................. 558/274, 277, 558/260

[56] References Cited

U.S. PATENT DOCUMENTS 5,214,184  5/1993  Matuzaki et al. ........................ 558/277
5,292,916  3/1994  Matsuzaki et al. ....................... 558/275

*Primary Examiner*—Samuel Barts
*Attorney, Agent, or Firm*—McAulay Fisher Nissen Goldberg & Kiel, LLP

[57] ABSTRACT

A porous lithium aluminate carrier for catalyst has a spinel structure which has a mean pore diameter in the range of 40 to 1,000 angstroms and a total pore volume in the range of 0.2 to 1.5 mL/g. The porous lithium aluminate carrier can be used for supporting a catalyst compound containing a platinum group metal. The catalyst on the carrier can be favorably employed for promoting catalytic reaction of a nitrite ester and carbon monoxide to prepare a carbonate diester such as dimethyl carbonate.

5 Claims, 3 Drawing Sheets

POROUS LITHIUM ALUMINATE CARRIER OF SPINEL STRUCTURE FOR CATALYST

FIELD OF THE INVENTION

The present invention relates to a porous lithium aluminate carrier of spinel structure for catalyst, a catalyst composition, a process for producing the porous lithium aluminate carrier, and a process for preparing a carbonate diester using the catalyst composition.

BACKGROUND OF THE INVENTION

A carbonate diester (e.g., dialkyl carbonate, dicycloalkyl carbonate, or diaralkyl carbonate) is utilized in industry for producing a therapeutically active compound or an agricultural chemical or producing polycarbonate or polyurethane. Heretofore, the carbonate diester has been prepared by causing a reaction between phosgene and an alcohol. This process, however, has disadvantages in that the toxic phosgene is necessarily employed as the starting compound and a corrosive hydrogen chloride is produced. A process for the preparation of a carbonic diester using no phosgene has already been developed. This process comprises a liquid-phase reaction between carbon monoxide and an alcohol in the presence of a copper halide catalyst or a palladium chloride catalyst. This process also has disadvantageous features in that carbon dioxide which is produced as by-product lowers selectivity on the carbon monoxide basis, and water which is also produced as by-product, makes it difficult to recover the yielded carbonate diester from the reaction mixture. Moreover, since the reaction is conducted in a liquid phase, it becomes necessary to separate the yielded carbonate diester from the catalyst. Therefore, this process appears unfavorable from the viewpoint of production of a carbonate diester in industry.

Japanese Patent Provisional Publication No. 60-81051 discloses a process for preparing a carbonate diester (i.e., diester of carbonic acid) in a gaseous phase by reacting carbon monoxide and a nitrite ester in the presence of a solid platinum group metal catalyst or a platinum group metal compound supported by a carrier using an oxidizing agent containing $O_2$ in an amount of 10 molar % per carbon monoxide. This process has a problem in that an oxalic acid diester, that is a by-product, is also produced not a small amount.

Japanese Patent Provisional Publications Nos. H3-141243 and H4-139152 disclose a process for preparing dimethyl carbonate by catalytic reaction between carbon monoxide and methyl nitrite in a gaseous phase in the presence of a catalytic composition which comprises a carrier such as active carbon or alumina and a catalytic element comprising a compound of metal of the platinum group such as palladium chloride or palladium sulfate and a compound of metal such as iron, copper, bismuth, cobalt, nickel, or a tin.

Japanese Patent Provisional Publication No. H4-89458 describes that employment of a small amount of hydrogen chloride in the above-mentioned process for the production of dimethyl carbonate using the catalyst composition which comprises a carrier such as active carbon or alumina and a catalytic element comprising a compound of metal of the platinum group and a compound of iron or the like is effective for keeping the activity of catalyst at a high level for a prolonged period of time.

EP-A-0 523 508 describes a process for producing a dialkyl carbonate by catalytic reaction from carbon monoxide and an alkyl nitrite in a gaseous phase in the presence of a halide of a metal of the platinum group or a complex compound containing a halide of a metal of the platinum group which is supported by a carrier of aluminum oxide, hydroxide of aluminum oxide, or aluminum hydroxide having a large specific surface area.

EP-464460B1 describes a process for producing a dialkyl carbonate by catalytic reaction between carbon monoxide and an alkyl nitrite in a gaseous phase which employs a catalyst comprising a carrier and a halide of a metal of the platinum group or a complex compound containing a halide of a metal of the platinum group which is modified by an element such as iron, cobalt, nickel or copper. The working examples described therein all employ alumina (i.e., aluminum oxide). The publication further has a description in that carriers which are generally employed for supporting a catalyst of the platinum group metal such as spinel, silicate, montomorillonite, zeolite, active carbon, molecular sieves, diatomaceous earth, silicone carbide, and silicone dioxide can be used.

SUMMARY OF THE INVENTION

It is a principal object of the present invention to provide a new catalyst carrier which is of great value particularly for supporting a catalyst comprising a compound of a metal of platinum group.

It is also an object of the invention to provide a catalyst composition comprising a carrier and a catalyst comprising a compound of a metal of platinum group which is favorably employable in the process for producing a carbonate diester such as dialkyl carbonate (e.g., methyl carbonate).

The present invention resides in a porous lithium aluminate carrier for catalyst which comprises a spinel structure having a mean pore diameter in the range of 40 to 1,000 angstroms and a total pore volume in the range of 0.2 to 1.5 mL/g.

The invention also resides in a catalyst composition which comprises the above-mentioned carrier and a catalyst component comprising a metal of platinum group or a compound of a metal of platinum group.

The invention further resides in a process for preparing the above-mentioned lithium aluminate carrier which comprises the steps of immersing an alumina powder having a specific area of 30 to 300 $m^2/g$ in an aqueous solution containing a lithium salt, recovering the immersed alumina powder from the solution, drying the recovered alumina powder, and calcining the dried alumina powder at a temperature of 500° to 1,000° C.

The invention further resides in a process for preparing the above-mentioned lithium aluminate carrier which comprises the steps of mixing an alumina sol and an aqueous solution containing a lithium salt, drying the resulting mixture, and calcining the dried mixture at a temperature of 500° to 1,000° C.

The invention furthermore resides in a process for the preparation of a carbonate ester such as dialkyl carbonate which comprises reacting a nitrite ester (e.g., an alkyl nitrite) and carbon monoxide in the presence of a catalyst composition which comprises a carrier of spinel structure having a mean pore diameter in the range of 40 to 1,000 angstroms and a total pore volume in the range of 0.2 to 1.5 mL/g and a catalyst component comprising a metal of platinum group or a compound of a metal of platinum group.

DETAILED DESCRIPTION OF THE INVENTION

Figure 1:
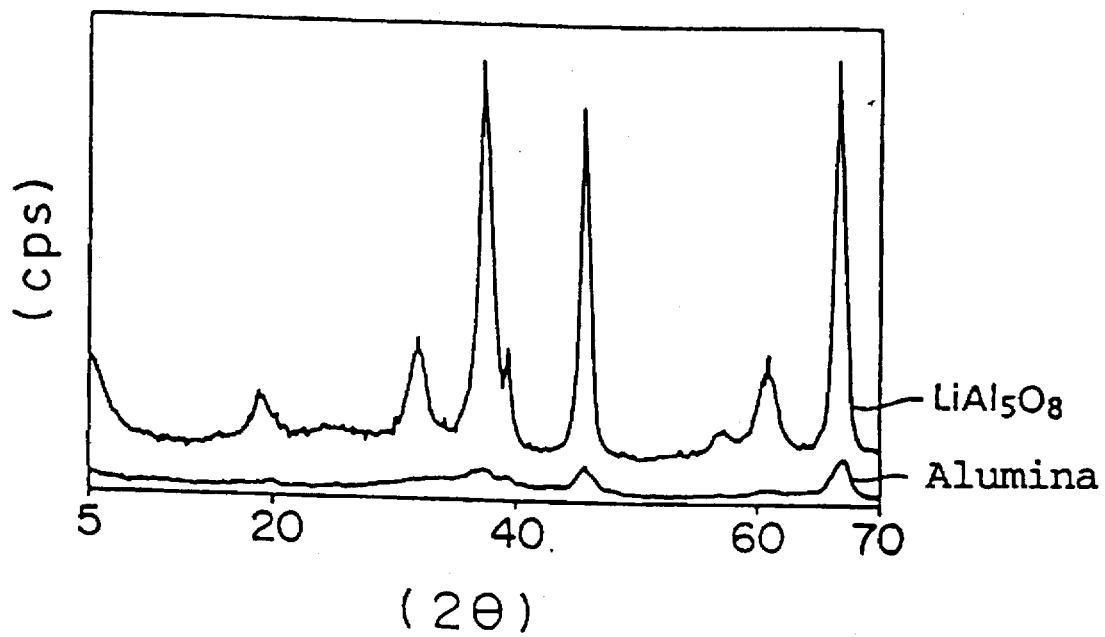
FIG. 1 is art X-ray diffraction chart of a porous lithium aluminate carrier of the invention.

The preferred embodiments of the present invention are described below:

A porous lithium aluminate carrier of the invention which comprises, as metal elements, lithium and aluminum under the condition that an atomic ratio of lithium/aluminum ranges from 0.2/5.0 to 1.5/5.0.

A porous lithium aluminate carrier of the invention which comprises, as metal elements, lithium and aluminum under the condition that an atomic ratio of lithium/aluminum ranges from 0.5/5.0 to 1.5/5.0.

A porous lithium aluminate carrier of the invention which has a formula of $Li_xAl_5O_{(15+x)/2}$, wherein x is a number of 0.5 to 1.5.

A porous lithium aluminate carrier of the invention which comprises, as metal elements, lithium, aluminum and a divalent metal under the condition that an atomic ratio of lithium/aluminum ranges from 0.2/5.0 to 1.5/5.0 and an atomic ratio of the divalent metal/aluminum is less than 2.0/5.0.

A porous lithium aluminate carrier of the invention which comprises, as metal elements, lithium, aluminum and a divalent metal under the condition that an atomic ratio of lithium/aluminum ranges from 0.2/5.0 to 1.3/5.0 and an atomic ratio of the divalent metal/aluminum ranges from 0.1/5.0 to 2.0/5.0.

A porous lithium aluminate carrier of the invention wherein the above-mentioned divalent metal is selected from the group consisting of magnesium, zinc, cobalt, nickel and copper.

A porous lithium aluminate carrier of the invention which has a formula of $Li_xMe_yAl_5O_{(15+x+2y)/2}$, wherein Me is a divalent metal, x is a number of 0.2 to 1.5, and y is a number of less than 2.0 under the condition that x+2y is a number of 0.5 to 5.0.

A porous lithium aluminate carrier of the invention which has a formula of $Li_xMe_yAl_5O_{(15+x+2y)/2}$, wherein Me is a divalent metal, x is a number of 0.2 to 1.5, and y is a number of 0.1 to 2.0 under the condition that x+2y is a number of 0.5 to 4.0.

A porous lithium aluminate carrier of the invention which has a specific surface area of 30 to 300 $m^2/g$, specifically 50 to 150 $m^2/g$.

A catalyst composition which comprises any of the above-mentioned carrier and a catalyst component comprising a metal of platinum group or a compound of a metal of platinum group.

A process for the preparation of a carbonate ester of the invention, wherein the reaction is performed further in the presence of a chlorine-containing gas.

A process for the preparation of a carbonate ester of the invention, wherein the reaction is performed further in the presence of hydrogen chloride.

[Catalyst Carrier]

The catalyst carrier of the invention which comprises a porous lithium aluminate body having a spinel structure is a new catalyst carrier. A spinel per se is a name of a complex oxide of magnesium and aluminum which is represented by $MgAl_2O_4$ or $MgO.Al_2O_3$, and is generally employed as a raw material of refractories.

The spinel structure is one of crystalline structures which is generally observed in compounds having the formula of $AB_2O_4$ (in which A and B independently are divalent or trivalent metal elements) and has an appearance of the hexagonal or nearly hexagonal structure. The spinel structure further has a cubic lattice in which the oxygen atoms are placed for forming the close-packed structure. Examples of compounds having the spinel structure include $MnAl_2O_4$, $FeAl_2O_4$, $ZnAl_2O_4$, $MgAl_2O_4$ and $ZnFe_2O_4$.

The porous lithium aluminate carrier of the spinel structure according to the invention has a pore diameter (mean value) in the range of 40 to 1,000 angstroms and a pore volume (i.e., total pore volume) in the range of 0.2 to 1.5 mL/g. The porous lithium aluminate catalyst carrier of the invention preferably comprises, as metal elements, lithium and aluminum under the condition that an atomic ratio of lithium/aluminum ranges from 0.2/5.0 to 1.5/5.0, more preferably from 0.5/5.0 to 1.5/5.0. A typical porous lithium aluminate carrier according to the invention has the formula of $Li_xAl_5O_{(15+x)/2}$, wherein x is a number of 0.5 to 1.5, preferably 0.7 to 1.3, more preferably 0.7 to 1.0. According to X-ray diffraction analysis, the porous lithium aluminate carrier of the formula has diffraction lines assigned to the spinel crystalline structure of $LiAl_5O_8$ only, or has diffraction lines assigned to the spinel crystalline structure of $LiAl_5O_8$ and diffraction lines assigned to the spinel crystalline structure of $LiAlO_2$.

Otherwise, the porous lithium aluminate carrier of the invention may comprise, as metal elements, lithium, aluminum and a divalent metal under the condition that an atomic ratio of lithium/aluminum ranges from 0.2/5.0 to 1.5/5.0 (specifically from 0.2/5.0 to 1.3/5.0) and an atomic ratio of the divalent metal/aluminum is less than 2.0/5.0 (specifically 0.1/5.0 to 2.0/5.0). The divalent metal is preferably selected from the group consisting of magnesium, zinc, cobalt, nickel and copper. A typical porous lithium aluminate carrier comprising metal elements of lithium, aluminum and a divalent metal has a formula of $Li_xMe_yAl_5O_{(15+x+2y)/2}$, wherein Me is a divalent metal, x is a number of 0.2 to 1.5, and y is a number of less than 2.0 (specifically 0.1 to 2.0) under the condition that x+2y is a number of 0.5 to 5.0 (specifically 0.5 to 4.0). According to X-ray diffraction analysis, the porous lithium aluminate carrier of the latter formula also has diffraction lines (d=1.39±0.10 Å, d=1.98±0.10 Å, and d=2.39±0.10Å) assigned to the spinel crystalline structure only, or consists essentially of diffraction lines assigned to the spinel crystalline structure.

The porous lithium aluminate catalyst carrier of the invention may have a defective spinel structure.

The porous lithium aluminate catalyst carrier of the invention can have the spinel structure only on the surface or in the vicinity of the surface area, and the core of the carrier may have other structure. The surface area of the carrier preferably has a strong acid site value of less than 0.1 mmol/g in which the strong acid site value is defined as a molar amount of adsorbed ammonia at which an adsorption heat of 90 kJ/mol or more is produced. The amount of adsorbed ammonia can be determined by a differential adsorption method described in "Surface" Vol. 20, No. 12, page 697 (1987) written by Kazuo Tutumi.

The porous lithium aluminate catalyst carrier of the invention generally has a specific surface area of not less than 30 $m^2/g$, preferably 30 to 300 $m^2/g$.

The preferred porous lithium aluminate catalyst carrier of the invention which has a large specific surface area imparts a high activity to a catalyst deposited thereon. Further, if the catalyst carrier of the invention having a weak surface acidity (that is, a small strong acid point value) is utilized in a catalytic reaction, unfavorable decomposition of the starting compound and unfavorable side-reactions are reduced.

The porous lithium aluminate catalyst carrier of the invention can be employed in the form of a powder, particles, and pellets. There is no specific limitation with respect to their sizes. The powder may have a body size of 20 to 100 μm. The particles may be of 4 to 200 mesh. The pellets may have a diameter in the range of 0.5 to 10 mm.

The porous lithium aluminate body of the invention can be produced by any of two processes, one of which comprises treating alumina powder with an aqueous solution containing a lithium salt and, if necessary, a salt of the divalent metal, and calcining the treated composition, and another of which comprises reaction of an alumina sol and an aqueous solution containing a lithium salt and, if necessary, a salt of the divalent metal, and calcining the reaction mixture. Details of these processes are described below.

In the first step of the process using the alumina powder, an alumina powder having a specific surface area of not less than 30 $m^2/g$ (preferably, 30 to 300 $m^2/g$) is immersed in an aqueous solution containing a lithium salt such as lithium nitrate or lithium hydroxide, and if necessary, a water-soluble salt of the divalent metal. The concentration of each of the lithium salt or divalent metal salt preferably is in the range of 1 to 5 mol/L, more preferably in the range of 1.5 to 3 mol/L. The amount of the alumina powder and the amount(s) of the lithium salt and the divalent metal salt are determined according to the desired composition of the porous lithium aluminate carrier. The aqueous solution in which the alumina powder is immersed is then treated in a rotary evaporator to distill water off, whereby having the aqueous salt solution adsorbed or deposited on the alumina powder. Thus treated alumina powder is dried under such conditions as a temperature of 40° to 200° C. and a period of 5 to 20 hours. The dried alumina powder which has on its surface the lithium salt, and optionally the divalent metal salt is then calcined at a temperature of higher than 500° C., preferably 500° to 1,000° C., more preferably 700° to 1,000° C., decomposing the metal salt and giving the desired porous lithium aluminate body having the spinel structure. The porous lithium aluminate body of the invention can be made in a controlled particle size by sieving the alumina or the treated alumina in an appropriate stage.

In the first step of the process starting from the alumina sol and the lithium salt (and optionally the divalent metal salt), an alumina sol and an aqueous solution containing a lithium salt and optionally the divalent metal salt. The amounts of the alumina sol and the lithium salt (and the divalent salt) are so adjusted as to give a desired composition. The aqueous mixture is then treated to distill water off and dried in the same manner as above, and calcined also in the same manner as above to give the desired porous lithium aluminate body having the spinel structure. In advance of the drying process, the aqueous mixture may be molded to give pellets of appropriate sizes and the resulting pellets can be dried and calcined to give the desired porous lithium aluminate body.

[Catalyst Composition]

The porous lithium aluminate body of the invention is favorably utilized as a catalyst carrier, because it can keep a catalyst composition deposited thereon at a high activity during a long reaction period. A representative example of the catalyst is a compound of a metal of the platinum group such as palladium chloride and palladium sulfate. The compound of platinum group metal can be utilized in combination with a compound of other metal such as iron, copper, bismuth, cobalt, nickel, or tin. The porous lithium aluminate carrier having thereon a catalyst composition of a compound of a metal of platinum group and a compound of other metal such as above can be favorably employed in the process for preparing a carbonate ester such as a dialkyl carbonate from a nitrite ester such as an alkyl nitrite and carbon monoxide.

The process for the preparation of a carbonate ester starting from a nitrite ester and carbon monoxide using the catalyst composition comprising a compound of a metal of platinum group and a compound of other metal deposited on the porous lithium aluminate carrier of spinel structure is further described below.

Examples of the metals of platinum group include palladium, platinum, iridium, ruthenium, and rhodium. Examples of the compounds of metals of platinum group include halides such as chloride, bromide, iodide, and fluoride, inorganic acid salts such as nitrate, sulfate, and phosphate, organic acid salts such as acetate and benzoate. Concrete examples are halides such as palladium chloride, palladium bromide, palladium iodide, palladium fluoride, lithium tetrachloropalladate, sodium tetrachloropalladate, potassium tetrachloropalladate, platinum chloride, iridium chloride, ruthenium chloride, ruthenium iodide, rhodium chloride, rhodium bromide, and rhodium iodide; inorganic acid salts such as palladium nitrate, palladium sulfate, palladium phosphate, rhodium nitrate, and rhodium sulfate; and organic acid salts such as palladium acetate, palladium benzoate, and rhodium acetate. Preferred are both halides and sulfates of palladium, ruthenium and rhodium. Most preferred is palladium chloride.

The chloride of the platinum group metal can be prepared in the reaction system. For instance, a metal per se or a metal compound which can be converted into a chloride or a chloro-containing compound upon contact with hydrogen chloride gas can be employed in place of the chloride.

The compound of the platinum group metal can be deposited on the porous lithium aluminate carrier of the present invention in the amount of 0.1 to 10 weight %, preferably 0.5 to 2 weight %, in terms of the amount of the metal, per the amount of the carrier.

As is described above, the compound of the platinum group metal can be employed in combination of other metal compound(s). For instance, any of iron, copper, bismuth, cobalt, nickel and tin can be employed in the form of halides such as chloride, bromide, iodide and fluoride, inorganic acid salts such as nitrate, sulfate and phosphate, and organic acid salts such as acetate. Vanadium, molybdenum, and tungsten can be also employed in combination in the form of their oxide, metallic acid or metallic acid salt such as vanadium oxide, molybdenum oxide, tungsten oxide, ammonium vanadate, ammonium molybdenate, and ammonium tungstenate. Further, lanthanoids metals such as lanthanum, cerium, praseodymium, neodymium, promethium, samarium, europium, gadolinium, terbium, thulium, ytterbium and lutetium can be incorporated into the catalyst composition in the form of metal compounds or metal salts such as their oxide, chloride, and nitrate.

These auxiliary metal compounds can be employed in combination with the platinum group metal compound in an amount of 0.1 to 50 gram atom equivalent, particularly 0.5 to 20 gram atom equivalent, in terms of metal atom equivalent to one gram metal atom equivalent of the platinum group metal in the platinum group metal compound. The catalyst composition comprising the porous lithium aluminate carrier and the catalytic element composition such as a platinum group metal compound has almost the same pore size and specific surface area as those of the employed porous lithium aluminate carrier.

[Production of Carbonate Diester]

The carbonate diester can be produced by catalytic reaction between a nitrite ester and carbon monoxide.

The nitrite ester can be selected from those known as the starting compound for the process for preparing a carbonate diester. Examples of the nitrite esters include nitrite esters of lower aliphatic monohydric alcohols having 1 to 4 carbon atoms such as methyl nitrite, ethyl nitrite, n-(or iso)propyl nitrite, and n-(or iso, or sec.-)butyl nitrite; nitrite esters of cyclic aliphatic alcohols having 5 to 8 carbon atoms such as cyclohexyl nitrite; nitrite esters of aralkyl alcohols such as benzyl nitrite. These nitrite esters can be produced by a process comprising the steps of producing a mixture of gaseous nitrogen monoxide (NO) and gaseous nitrogen dioxide ($NO_2$) by decomposition of sodium nitrite by nitric acid or sulfuric acid in an aqueous phase; oxidizing a portion of NO in the gaseous mixture by molecular oxygen to convert it into $NO_2$ whereby obtaining a gaseous $NO_x$ in which $NO/NO_2$ is 1/1 (volume ratio); and bringing the gaseous mixture into contact with an alcohol; or the steps of recovering NO produced in the reaction for the production of a carbonate diester from a nitrite ester and carbon monoxide and bringing the recovered NO into contact with an alcohol and oxygen to produce a nitrite ester.

In the production of a carbonate diester in industry, it is preferred that the process for the production of a nitrite ester and the process of the catalytic reaction between the nitrite ester and carbon monoxide are continuously performed.

The catalytic reaction between the nitrite ester and carbon monoxide can be performed in a gaseous phase or a liquid phase and in a batch process or a continuous process. In industry, the reaction according to the continuous process in a gaseous phase is preferably adopted. The catalyst composition can be employed in any of optional bed such as a solid bed or a fluid bed. The reaction conditions such as the reaction temperature for the catalytic reaction can be selected from the known conditions. For instance, the reaction temperature can be between 0° and 200° C., preferably between 50° and 140° C. The reaction pressure can be an atmospheric pressure. The reaction also can be performed under pressure at 1 to 20 kg/cm².

In the gaseous mixture of a nitrite ester and carbon monoxide for the production of the carbonate diester, carbon monoxide is preferably contained in an amount of 0.1 to 10 mol., preferably 0.25 to 1 mol., based on 1 mol. of the nitrite ester. The gaseous mixture is fed into a reaction vessel or area generally at a space velocity of 500 to 20,000 hr$^{-1}$, preferably 2,000 to 15,000 hr$^{-1}$. In the reaction, the gaseous mixture of a nitrite ester and carbon monoxide is preferably employed after it is diluted with an inert gas such as nitrogen gas. There is no specific limitation with respect to the amount of a diluent gas. However, the concentration of nitrite ester in the gaseous mixture to be fed into the reaction vessel or area is preferably adjusted to 5 to 20 volume %, from the viewpoints of safety and reaction efficiency.

A portion of carbon monoxide can be employed in the gaseous mixture to be fed to the reaction vessel or area. In that case, the amount of carbon monoxide in the gaseous mixture can be increased up to 80 volume %. However, the amount of carbon monoxide preferably is in the range of 5 to 20 volume %. This is because the gaseous mixture preferably is continuously fed into the reaction vessel or area in cycle in the industrial production; a portion of the recycled gaseous mixture is preferably purged from the reaction system; the conversion ratio of carbon monoxide in one pass (each cycle) generally is in the range of 20 to 30%; therefore, a higher concentration of carbon monoxide such as more than 20 volume % is not effective to increase the yield of the carbonate diester; and a lower concentration such as lower than 5 volume % causes decrease of a production efficiency.

Into the reaction vessel or area for the production of a carbonate diester, a chlorine-containing gas such as hydrogen chloride or a chloroformate ester is preferably fed together with the nitrite ester and carbon monoxide. The use of hydrogen chloride or chloroformate is effective to keep the activity of the catalyst at a high level. Hydrogen chloride preferably is anhydrous hydrogen chloride. The chloroformate ester can be an ester of chloroformic acid and a lower aliphatic monohydric alcohol having 1 to 4 carbon atoms such as methyl chloroformate, ethyl chloroformate, n-(or iso)-propyl-chloroformate, an ester of chloroformic acid and an alicyclic alcohol having 5 to 8 carbon atoms such as cyclohexyl chloroformate, and an ester of chloroformic acid and an aralkyl alcohol such as benzyl chloroformate. If a chloroformate ester is employed for the production of a dialkyl carbonate from an alkyl nitrite, such chloroformate ester preferably is an ester of an alcohol which has the same alkoxy group of the alkyl nitrite.

Hydrogen chloride or chloroformate ester can be introduced in any known way into the reaction area. For instance, it is preferred that a small amount of hydrogen chloride or chloroformate ester is continuously fed into the reaction area in the way described below.

1) Hydrogen chloride

If a large amount of hydrogen chloride is introduced into the reaction area, not a small amount of hydrogen chloride is adsorbed by the catalytic composition and the desired catalytic reaction is disturbed. Therefore, hydrogen chloride is preferably added to the gaseous mixture to be continuously fed into the reaction area in an amount of less than 1,000 volume ppm, preferably 5 to 500 volume ppm, more preferably 10 to 300 volume ppm.

2) Chloroformate ester

There also is no specific limitation with respect to the amount of chloroformate ester to be fed into the reaction area. However, since the use of an excessive amount of chloroformate ester is disadvantageous from the economic viewpoint, the chloroformate ester is preferably added to the gaseous mixture in an amount of less than 1 volume %, more preferably less than 1,000 volume ppm. The addition of chloroformate ester to the gaseous mixture can be done, for instance, by the following method: a nitrogen gas is passed through a warmed chloroformate ester whereby vapor of the chloroformate ester is carried with the nitrogen gas into the gaseous mixture to be continuously fed into the reaction area. The chloroformate ester can be directly fed into the reaction area together with a carrier gas such as nitrogen gas.

The reaction of a nitrite ester and carbon monoxide in the presence of a catalyst composition comprising mainly the platinum group metal compound yields the desired carbonate diester. The produced carbonate diester is then recovered from the reaction mixture. In the recovery of the carbonate diester, by-products such as an oxalate diester and unreacted carbon monoxide and nitrite ester, and further nitrogen monoxide which was contained in the gaseous mixture fed into the reaction area are also recovered. The desired carbonate diester can be isolated and purified by known methods such as distillation after condensation by chilling. A mixture of carbon monoxide, nitrite ester, and nitrogen monoxide which are not easily condensated can be recycled into the starting gaseous mixture by feeding to the gaseous mixture or into the reaction area.

In the above descriptions, the porous lithium aluminate carrier of spinel structure according to the invention are described for the use of supporting a compound of a platinum group metal which is favorably employed for the production of a carbonate diester from a nitrite ester and carbon monoxide. It should be understood, however, that the porous lithium aluminate carrier of the invention can be employed for supporting other catalyst compositions. Such catalyst compositions can be advantageously employed for promoting a variety of catalytic reactions.

The present invention is further described by the following examples.

EXAMPLE 1

In an aqueous lithium nitrate solution (concentration: 1.96 mol./L) was immersed 30 g of a commercially available alumina catalyst carrier (spherical, mean diameter: 2 mm, specific surface area: 193 m²/g). The aqueous mixture was kept for one hour and placed in a rotary evaporator for distilling water off. The residue was heated at 110° C. for 10 hours in air for dryness to obtain an alumina body on which lithium nitrate was deposited. The alumina body carrying lithium nitrate thereof was heated at 350° C. for one hour in air to decompose the lithium nitrate, and successively calcined in air at 500° C. for 3.5 hours and at 800° C. for 5 hours. Thus, a porous lithium aluminate (LiAl$_5$O$_8$) having Li/Al of 1/5 (atomic ratio) was obtained.

FIG. 1 is an X-ray diffraction chart (X-ray source: Cu-Kα) of the obtained porous lithium aluminate. The X-ray diffraction chart indicates that the obtained porous lithium aluminate has a spinel structure.

The pore size distribution and mean pore size of the obtained porous lithium aluminate were then measured by means of a mercury porosimeter. It was confirmed that the pore sizes were in the range of 40 to 2,000 angstroms and the mean pore diameter was 248 angstroms. The pore volume was 0.48 mL/g, and the BET specific surface area was 57 m²/g.

EXAMPLES 2 TO 6

The procedures of Example 1 were repeated except for varying the amounts of the alumina body and the aqueous lithium nitrate solution to obtain porous lithium aluminates having different Li/Al values. The mean pore diameters and pore volumes of the porous lithium aluminates are given in Table 1. According to the X-ray diffraction analysis, it was confirmed that each of the obtained porous lithium aluminates had the spinel structure.

TABLE 1

| Example No. | Li/Al (atomic) | Mean pore diameter (Å) | Pore volume (mL/g) | BET surface area (m²/g) |
|---|---|---|---|---|
| 1 | 1.0/5.0 | 248 | 0.48 | 57 |
| 2 | 0.7/5.0 | 162 | 0.47 | 96 |
| 3 | 0.8/5.0 | 175 | 0.46 | 91 |
| 4 | 0.9/5.0 | 202 | 0.46 | 84 |
| 5 | 1.15/5.0 | 275 | 0.45 | 52 |
| 6 | 1.3/5.0 | 266 | 0.44 | 58 |

EXAMPLE 7

In 300 mL of pure water was dissolved 8.115 g of lithium nitrate (LiNO$_3$). The resulting aqueous solution was warmed on a water bath kept at 60° C. To the warmed solution was portionwise added 150 g of alumina sol (containing 20 wt.% of Al$_2$O$_3$, tradename: Alumina sol-520, product of Nissan Chemical Co., Ltd.) under stirring. The stirring was continued for 1 hour for aging. The resulting thick slurry was placed in a rotary evaporator to distill excessive water off. The residue was extruded to give particles. The particles were successively dried in air at 60° C. for 16 hours and 110° C. for 10 hours. The dried particles were sieved to adjust their particle diameters of 3 mm and length of 4 mm. Thus treated particles were heated at 350° C. for one hour to decompose the nitrate ingredient, and successively calcined in air at 500° C. for 3 hours and at 700° C. for 5 hours. Thus, a porous lithium aluminate (LiAl$_5$O$_8$) having Li/Al of 1/5 (atomic ratio) was obtained.

Figure 2:
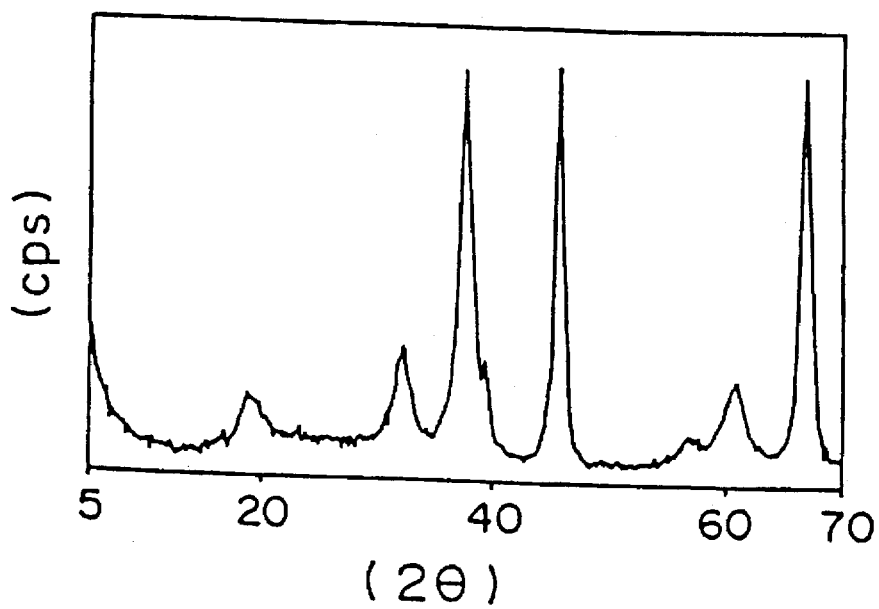
FIG. 2 is an X-ray diffraction chart of another porous lithium aluminate carrier of the invention.

FIG. 2 is an X-ray diffraction chart (X-ray source: Cu-Kα) of the obtained porous lithium aluminate. The X-ray diffraction chart indicates that the obtained porous lithium aluminate has a spinel structure.

The pore size distribution and mean pore size of the obtained porous lithium aluminate were then measured by means of a mercury porosimeter. It was confirmed that the pore sizes were in the range of 50 to 260 angstroms and the mean pore diameter was 144 angstroms. The pore volume was 0.30 mL/g, and the BET specific surface area was 80 m²/g.

EXAMPLE 8

The procedures of Example 7 were repeated except that 6.492 g of lithium nitrate was employed and the calcining procedure was performed at 800° C., to give a porous lithium aluminate (Li$_{0.8}$Al$_5$O$_{7.9}$) having Li/Al of 0.8/5.0 (atomic ratio).

The X-ray diffraction chart of the obtained porous lithium aluminate had the same pattern as that of FIG. 2. Thus, it was confirmed that the obtained porous lithium aluminate had the spinel structure.

The pore size distribution and mean pore size of the obtained porous lithium aluminate were then measured by means of a mercury porosimeter. It was confirmed that the pore sizes were in the range of 40 to 200 angstroms and the mean pore diameter was 111 angstroms. The pore volume was 0.31 mL/g, and the BET specific surface area was 102 m²/g.

COMPARISON EXAMPLE 1

The commercially available alumina which was the same as that employed for the preparation of the porous lithium aluminate having the spinel structure in Example 1 was obtained.

COMPARISON EXAMPLE 2

The procedures of Example 7 were repeated except for employing lithium nitrate, to give alumina particles of amorphous structure which showed no strong peaks in the X-ray diffraction chart. The pore diameter distribution was within the range of 50 to 200 angstroms (Å). The mean pore diameter was 95 Å; the pore volume was 0.32 mL/g, and the BET specific surface area was 140 m$^2$/g.

EXAMPLE 9

Each of the porous lithium aluminate bodies (that is, catalyst carriers) obtained in Examples 1–4 and 7 and each of the alumina bodies (catalyst carriers) obtained in Comparison Examples 1 and 2 was treated in an aqueous ammonia solution containing palladium chloride and cupric chloride to deposit 1 wt. % of palladium and 1.2 wt. % of copper thereon. Thus treated carrier was dried at 110° C. and calcined at 200° C. in air to produce a catalyst composition having palladium chloride and cupric chloride thereof.

Methyl nitrite and carbon monoxide were reacted in the presence of the above-obtained solid catalyst composition to produce dimethyl carbonate in a gaseous phase reaction apparatus of fixed bed type. The reaction conditions are described below, and the results are set forth in Table 2.

Gaseous mixture fed into the apparatus:
  methyl nitrite: 20 vol. %
  carbon monoxide: 5 vol. %
  hydrogen chloride: 100 ppm
  remainder: diluent gas (nitrogen gas)
Gas feeding conditions:
  feeding rate (space velocity, in terms of STP): 10,000 hr$^{-1}$
  pressure: 3 kg/cm$^2$ G
Reaction temperature: 120° C.
Reaction period: 6 hours
Amount of catalyst: 1.4 g (2.0 mL)

TABLE 2

| Catalyst | Conversion Ratio (%) | | Space Time Yield (g/L · hr) | | Selectivity (%) to DMC | |
| --- | --- | --- | --- | --- | --- | --- |
| Carrier | per CO | per MN | DMC | DMO | per CO | per MN |
| Example 1 | 55 | 34 | 715 | 14 | 94 | 91 |
| Example 2 | — | 38 | 1036 | 9.6 | 96 | 93 |
| Example 3 | — | 41 | 1096 | 7.1 | 96 | 92 |
| Example 4 | 64 | 35 | 855 | 10 | 96 | 95 |
| Comp. Ex. 1 | 42 | 29 | 627 | 4.2 | 93 | 88 |
| Example 7 | 52 | 36 | 793 | 6.8 | 94 | 91 |
| Comp. Ex. 2 | 51 | 30 | 398 | 4.1 | 90 | 85 |

Remarks: CO: carbon monoxide, DMC: dimethyl carbonate MN: methyl nitrite, DMO: dimethyl oxalate Further, in order to examine durability of the solid catalyst compositions prepared using the porous lithium aluminate carriers of the spinel structure (Examples 1 to 4 and 7), the above-mentioned reactions were continued for 40 days (960 hours). There was observed no significant lowering of the conversion ratio and the space time yield (STY) in the reaction using each catalyst composition.

EXAMPLE 10

The porous lithium aluminate body (catalyst carrier) obtained in Example 8 was treated with the aqueous ammonia solution containing palladium chloride and cupric chloride to deposit 1 wt. % of palladium and 1.2 wt. % of copper thereon. Thus treated carrier was dried at 110° C. and calcined at 200° C. in air to produce a catalyst composition having palladium chloride and cupric chloride thereon.

Methyl nitrite and carbon monoxide were reacted in the presence of the resulting catalyst composition to produce dimethyl carbonate in a gaseous phase reaction apparatus of fixed bed type. The reaction conditions are described below, and the results are given in Table 3.

Gaseous mixture fed into the apparatus:
  methyl nitrite: 15 vol. %
  carbon monoxide: 10 vol. %
  hydrogen chloride: 100 ppm
  remainder: diluent gas (nitrogen gas)
Gas feeding conditions:
  feeding rate (space velocity, in terms of STP): 3,000 hr$^{-1}$
  pressure: 3 kg/cm$^2$ G
Reaction temperature: 120° C.
Reaction period: 21 hours
Amount of catalyst: 6.7 mL

TABLE 3

| Catalyst | Conversion Ratio (%) | | Space Time Yield (g/L · hr) | | Selectivity (%) to DMC | |
| --- | --- | --- | --- | --- | --- | --- |
| Carrier | per CO | per MN | DMC | DMO | per CO | per MN |
| Example 8 | 63 | 82 | 623 | 10 | 95 | 96 |

Remarks: CO, DMC, MN and DMO have the same meaning as in Table 2.

Further, in order to examine durability of the above solid catalyst composition, the reaction was continued for 500 hours. There was observed no significant lowering of the conversion ratio and the space time yield (STY) in the reaction.

EXAMPLE 11

In 300 mL of pure water were dissolved 5.766 g of lithium nitrate (LiNO$_3$) and 13.40 g of magnesium nitrate (Mg(NO$_3$)$_2$·6H$_2$O). The resulting aqueous solution was warmed on a water bath kept at 60° C. To the warmed solution was portionwise added 133.40 g of alumina sol (containing 20 wt. % of Al$_2$O$_3$, tradename: Alumina sol-520, product of Nissan Chemical Co., Ltd.) under stirring. The stirring was continued for 1 hour for aging. The resulting thick slurry was placed in a rotary evaporator to distill excessive water off. The residue was extruded to give particles. The particles were successively dried in air at 60° C. for 16 hours and 110° C. for 10 hours. Thus obtained particles were heated at 350° C. for one hour to decompose and remove the nitrate ion, and successively calcined in air at 800° C. for 5 hours. Thus, a porous lithium magnesium aluminate (Li$_{0.8}$Mg$_{0.5}$Al$_5$O$_{8.4}$) was obtained.

Figure 3:
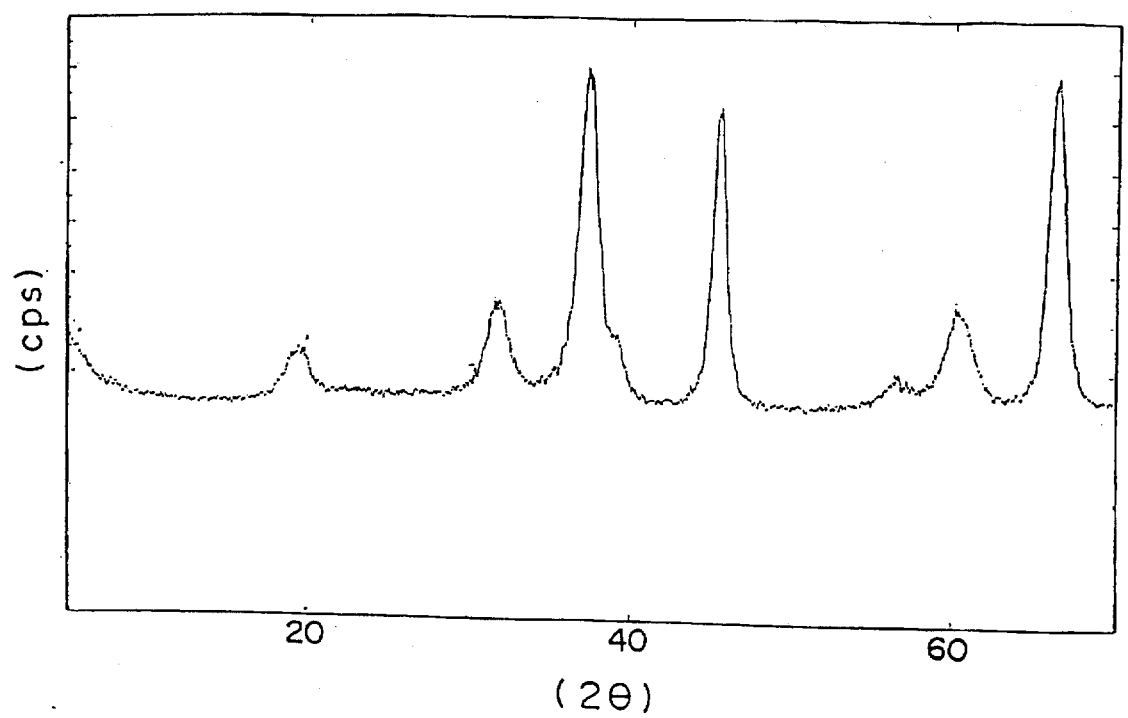
FIG. 3 is an X-ray diffraction chart of a porous lithium aluminate carrier comprising a divalent metal which also embodies of the invention.

FIG. 3 illustrates an X-ray diffraction chart (X-ray source: Cu-Kα) of the obtained porous lithium magnesium aluminate. The chart shows strong peaks at diffraction angles 2θ=37.3° (plane space d=2.41 Å), 45.5° (d=1.99 Å), 66.3° (d=1.41 Å). This means that the obtained porous lithium magnesium aluminate has a spinel structure.

The pore size distribution and mean pore size of the obtained porous lithium magnesium aluminate of complex type were then measured by means of a mercury porosimeter. It was confirmed that the pore sizes were in the range of 44 to 340 angstroms and the mean pore diameter was 153 angstroms. The pore volume was 0.25 mL/g, and the BET specific surface area was 66 m²/g.

EXAMPLES 12 TO 13

The procedures of Example 11 were repeated except that the amounts of lithium nitrate and magnesium nitrate were varied, to give a porous lithium magnesium aluminate of Example 12 ($Li_{0.6}Mg_{0.4}Al_5O_{8.2}$) and a porous lithium magnesium aluminate of Example 13 ($Li_{0.6}Mg_{0.2}Al_5O_8$).

The X-ray diffraction charts of the obtained porous lithium magnesium aluminates had the same pattern as that of FIG. 3. Thus, it was confirmed that the obtained porous lithium magnesium aluminates had the spinel structure.

The mean pore size, pore volume and BET specific surface area of each of the obtained porous lithium magnesium aluminates are set forth in Table 4.

EXAMPLES 14 TO 16

The procedures of Example 11 were repeated except that magnesium nitrate was replaced with zinc nitrate ($Zn(NO_3)_2 \cdot 6H_2O$) and the ratio of lithium nitrate, zinc nitrate and alumina sol was varied, to give porous lithium zinc aluminates of Example 14 ($Li_{0.8}Zn_{0.5}Al_5O_{8.4}$), Example 15 ($Li_{0.6}Zn_{0.4}Al_5O_{8.2}$), and Example 16 ($Li_{0.8}Zn_{0.2}Al_5O_8$).

The X-ray diffraction charts of the obtained porous lithium zinc aluminates had the same pattern as that of FIG. 3. Thus, it was confirmed that the obtained porous lithium zinc aluminates had the spinel structure.

The mean pore size, pore volume and BET specific surface area of each of the obtained porous lithium zinc aluminates are set forth in Table 4.

EXAMPLES 17 TO 19

The procedures of Example 11 were repeated except that magnesium nitrate was replaced with cobalt nitrate ($Co(NO_3)_2 \cdot 6H_2O$), nickel nitrate ($Ni(NO_3)_2 \cdot 6H_2O$), or copper nitrate ($Cu(NO_3)_2 \cdot 6H_2O$), to give a porous lithium cobalt aluminate of Example 17 ($Li_{0.6}Co_{0.2}Al_5O_8$), a porous lithium nickel aluminate of Example 18 ($Li_{0.6}Co_{0.2}Al_5O_8$), and a porous lithium copper aluminate of Example 19 ($Li_{0.6}Cu_{0.2}Al_5O_8$).

The X-ray diffraction chart of the obtained porous lithium cobalt (or nickel or copper) aluminate had the same pattern as that of FIG. 3. Thus, it was confirmed that the obtained porous lithium cobalt (or nickel or copper) aluminate had the spinel structure.

The mean pore size, pore volume and BET specific surface area of each of the obtained porous lithium cobalt (or nickel or copper) aluminates are set forth in Table 4.

TABLE 4

| Example No. | Lithium Aluminate | Mean pore diameter (Å) | Pore volume (mL/g) | BET surface area (m²/g) |
|---|---|---|---|---|
| 11 | $Li_{0.8}Mg_{0.5}Al_5O_{8.4}$ | 153 | 0.25 | 66 |
| 12 | $Li_{0.6}Mg_{0.4}Al_5O_{8.2}$ | 144 | 0.29 | 81 |
| 13 | $Li_{0.6}Mg_{0.2}Al_5O_8$ | 127 | 0.32 | 99 |
| 14 | $Li_{0.8}Zn_{0.5}Al_5O_{8.4}$ | 245 | 0.29 | 48 |
| 15 | $Li_{0.6}Zn_{0.4}Al_5O_{8.2}$ | 167 | 0.27 | 67 |
| 16 | $Li_{0.8}Zn_{0.2}Al_5O_8$ | 139 | 0.23 | 84 |
| 17 | $Li_{0.6}Co_{0.2}Al_5O_8$ | 127 | 0.31 | 98 |
| 18 | $Li_{0.6}Ni_{0.2}Al_5O_8$ | 125 | 0.30 | 97 |
| 19 | $Li_{0.6}Cu_{0.2}Al_5O_8$ | 136 | 0.28 | 81 |

EXAMPLE 20

Each of the porous lithium aluminate bodies (that is, catalyst carriers) obtained in Examples 11 to 19 was treated in an aqueous ammonia solution containing palladium chloride and cupric chloride to deposit 1 wt. % of palladium and 1.2 wt. % of copper thereon. Thus treated carrier was dried at 110° C. and calcined at 200° C. in air to produce a catalyst composition having palladium chloride and cupric chloride thereon.

Methyl nitrite and carbon monoxide were reacted in the presence of the above-obtained solid catalyst composition to produce dimethyl carbonate in a gaseous phase reaction apparatus of fixed bed type. The reaction conditions are described below, and the results are set forth in Table 5.

Gaseous mixture fed into the apparatus:
  methyl nitrite: 20 vol. %
  carbon monoxide: 5 vol. %
  hydrogen chloride: 100 ppm
  remainder: diluent gas (nitrogen gas)
Gas feeding conditions:
  feeding rate (space velocity, in terms of STP): 3,000 hr$^{-1}$
  pressure: 3 kg/cm² G
Reaction temperature: 120° C.
Reaction period: 6 hours
Amount of catalyst: 1.4 g (2.0 mL)

TABLE 5

| Catalyst Carrier | Conversion Ratio (%) | | Space Time Yield (g/L · hr) | | Selectivity (%) to DMC | |
|---|---|---|---|---|---|---|
| | per CO | per MN | DMC | DMO | per CO | per MN |
| Example 11 | 47 | 64 | 464 | 26 | 90 | 93 |
| Example 12 | 65 | 89 | 656 | 14 | 94 | 95 |
| Example 13 | 66 | 88 | 649 | 11 | 92 | 96 |
| Example 14 | 54 | 74 | 536 | 14 | 94 | 94 |
| Example 15 | 63 | 87 | 657 | 11 | 94 | 95 |
| Example 16 | 61 | 83 | 637 | 15 | 94 | 94 |
| Example 17 | 64 | 85 | 609 | 12 | 92 | 95 |
| Example 18 | 53 | 73 | 509 | 8 | 92 | 96 |
| Example 19 | 55 | 71 | 517 | 32 | 87 | 91 |

Remarks: CO: carbon monoxide, DMC: dimethyl carbonate
MN: methyl nitrite, DMO: dimethyl oxalate Further, in order to examine durability of the solid catalyst compositions prepared using the porous lithium aluminate carriers of the spinel structure (Examples 11 to 19), the above-mentioned reactions were continued for 40 days (960 hours). There was observed no significant lowering of the conversion ratio and the space time yield (STY) in the reaction using each catalyst composition.

EXAMPLE 21

The porous lithium magnesium aluminate obtained in Example 11 was measured on its surface acid site value in the following, manner according to an ammonia differential adsorption method (reference: "Surface", vol. 20, No. 12, p.697 (1987), written by Kazuo Tutumi): A sample (approximately 0.5 g) is placed under vacuum at 200° C. for degassing, and approximately 0.003 mmol of ammonia/each time (that is, ammonia pulse) is successively adsorbed on the degassed sample at room temperature. The produced adsorption heat is then measured in terms of a differential adsorption heat.

Figure 4:
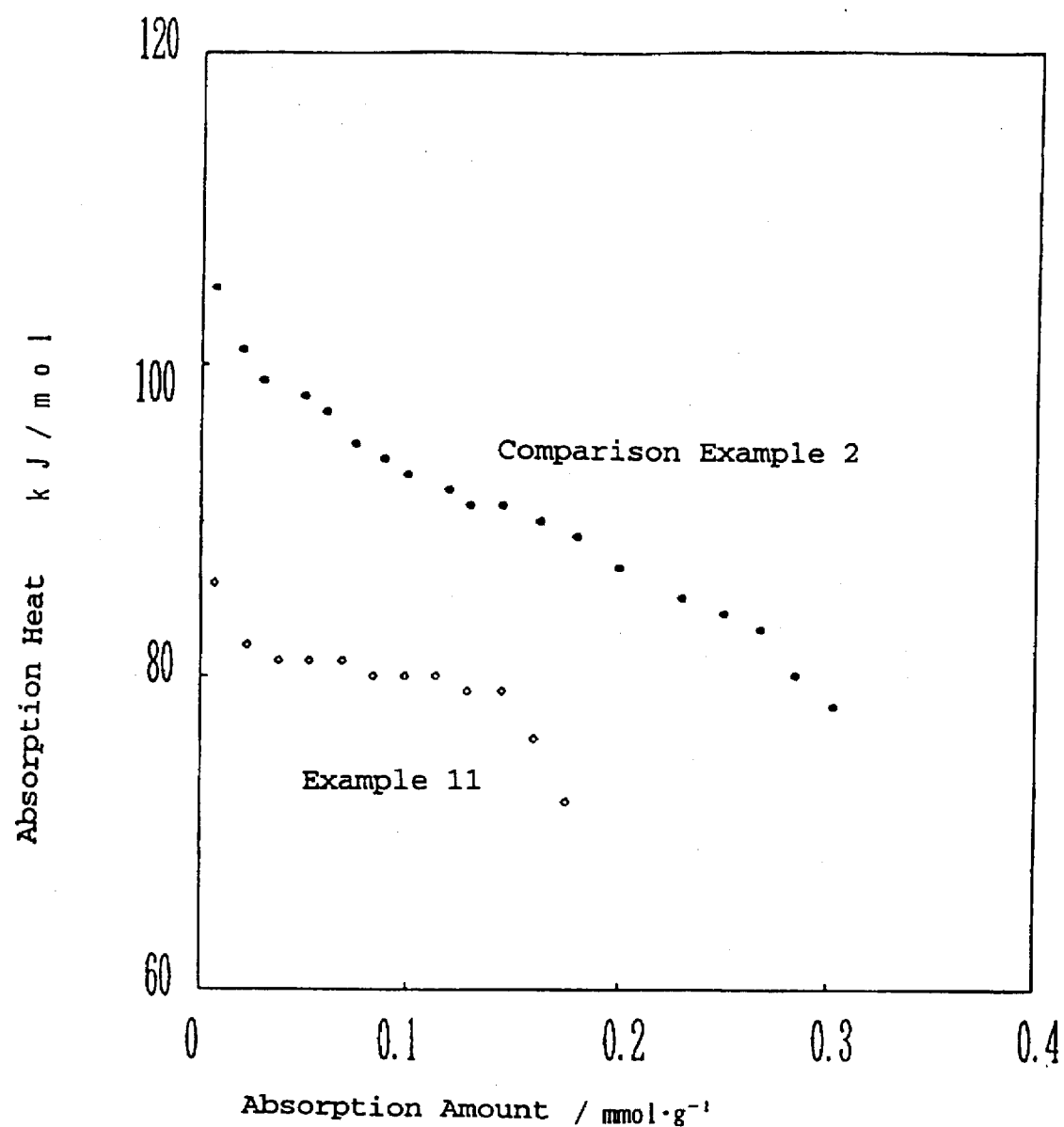
FIG. 4 shows a graph of differential adsorption heat from which the strong acid site values are determined.

The obtained differential adsorption heat is illustrated in FIG. 4 in the form of a graph. This graph means that the strong acid site values showing an adsorption sites of higher than 90 kJ/mol is 0.00 mmol/g.

The porous lithium aluminate body of Example 8 was. also subjected to the measurement of the strong acid site value and given 0.007 mmol/g as the strong acid site value.

The porous alumina body of Comparison Example 2 was also subjected to the measurement of the strong acid point and given 0.017 mmol/g as the strong acid point value.

What is claimed is:

1. A process for the preparation of a carbonate diester which comprises reacting a nitrite ester and carbon monoxide in the presence of a catalyst composition which comprises a carrier of a spinel structure having a mean pore diameter in the range of 40 to 1,000 angstroms and a total pore volume in the range of 0.2 to 1.5 mL/g and a catalyst component comprising a compound of a metal of platinum group.

2. The process for the preparation of a carbonate diester of claim 1, in which the carbonate diester is a dialkyl carbonate and the nitrite ester is an alkyl nitrite.

3. The process for the preparation of a carbonate diester of claim 1, in which the carbonate diester is dimethyl carbonate and the nitrite ester is methyl nitrite.

4. The process of claim 1, wherein the reaction is performed further in the presence of a chlorine-containing gas.

5. The process of claim 1, wherein the reaction is performed further in the presence of hydrogen chloride.

* * * * *

UNITED STATES PATENT AND TRADEMARK OFFICE
CERTIFICATE OF CORRECTION

PATENT NO. : 5,688,984
ISSUED : November 18, 1997
INVENTOR(S): Kyoji OHDAN et al It is certified that this error appears in the above-identified patent and that said Letters Patent is hereby corrected as shown below:

Column 1, line 54, before "tin" delete "a";

Column 2, line 16, change "montomorillo-" to --montmorillo- --;

line 17, change "silicone" to --silicon-- both occurrences.;

Signed and Sealed this

Ninth Day of June, 1998

*Attest:*

BRUCE LEHMAN

*Attesting Officer*       *Commissioner of Patents and Trademarks*